United States Patent
Jensen et al.

(10) Patent No.: US 6,375,461 B1
(45) Date of Patent: Apr. 23, 2002

(54) GINGIVAL RETRACTION CORDS INCORPORATING PROPYLHEXEDRINE

(75) Inventors: Steven D. Jensen, Riverton; Dan E. Fischer, Sandy, both of UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/664,142

(22) Filed: Sep. 18, 2000

(51) Int. Cl.[7] .................................................. A61C 5/12
(52) U.S. Cl. ........................................................ 433/136
(58) Field of Search .............................. 433/136, 138, 433/139, 215; 132/325

(56) References Cited

U.S. PATENT DOCUMENTS

| | | | |
|---|---|---|---|
| 2,454,746 A | 11/1948 | Ullyot | 260/563 |
| 4,321,038 A | 3/1982 | Porteous | 433/136 |
| 4,465,462 A | 8/1984 | Ticknor | 433/136 |
| 4,522,593 A | 6/1985 | Fischer | 433/136 |
| 4,522,933 A | 6/1985 | Abatjoglou et al. | 502/161 |
| 4,617,950 A | 10/1986 | Porteous et al. | 132/91 |
| 4,871,311 A | 10/1989 | Hagne | 433/136 |
| 4,892,482 A | 1/1990 | Lococo | 433/136 |
| 5,540,588 A | 7/1996 | Earle | 433/136 |
| 5,635,162 A | 6/1997 | Fischer | 424/49 |
| 5,750,141 A | 5/1998 | Roberts et al. | |
| 5,899,694 A | 5/1999 | Summer | 433/136 |

Primary Examiner—John J. Wilson
Assistant Examiner—Melba Bumgarner
(74) Attorney, Agent, or Firm—Workman, Nydegger & Seeley

(57) ABSTRACT

Gingival retracting cords including propylhexedrine (e.g., propylhexedrine HCI) for providing hemostasis and retraction or displacement of gingival tissue. The retraction cords include a hemostatic and tissue stiffening and retraction effective amount of propylhexedrine which avoids the negative side effects associated with the use of epinephrine, commonly used in conventional retraction cords. Retraction cords incorporating propylhexedrine do not cause increased blood pressure or accelerated heart rate. In addition, such retraction cords may include astringents, such as iron (III) salts without causing discoloration of the retraction cord, the patient's teeth or gums, or the fingers of the dental practitioner, as would occur if one were to blend epinephrine with iron (III) salts. Water or other appropriate solvents may be used to impregnate, or otherwise treat, the retraction cord with propylhexedrine (e.g., propylhexedrine HCI).

20 Claims, 2 Drawing Sheets

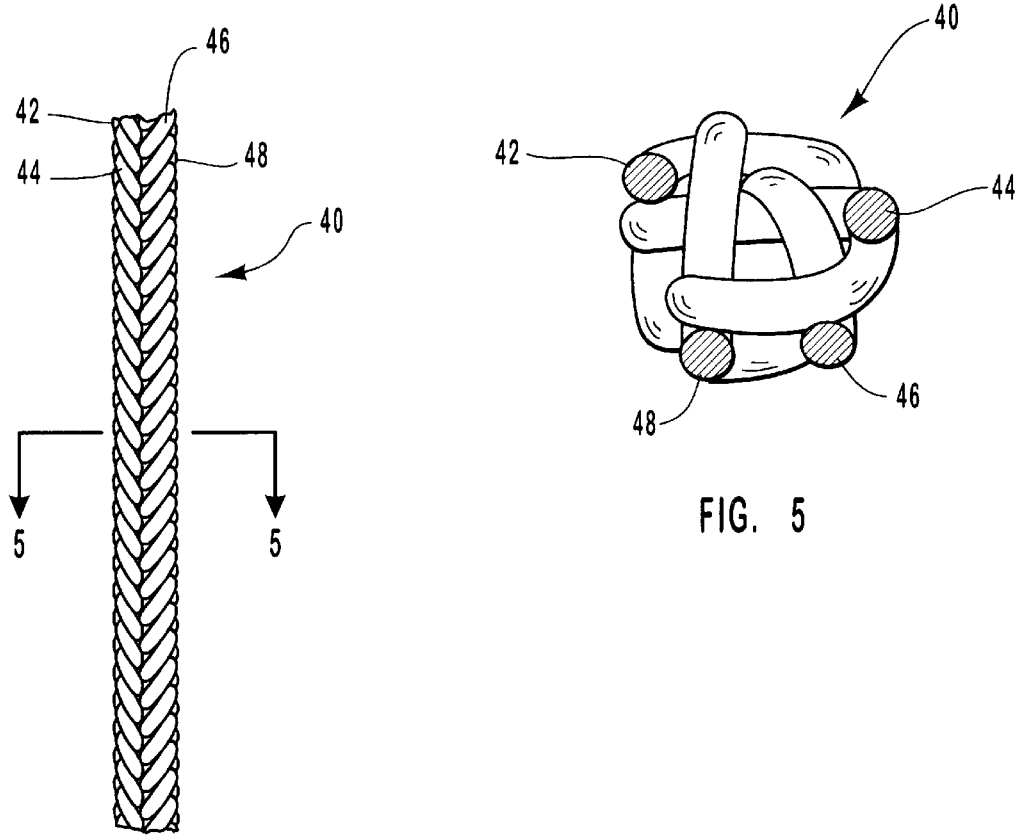
FIG. 4
FIG. 5
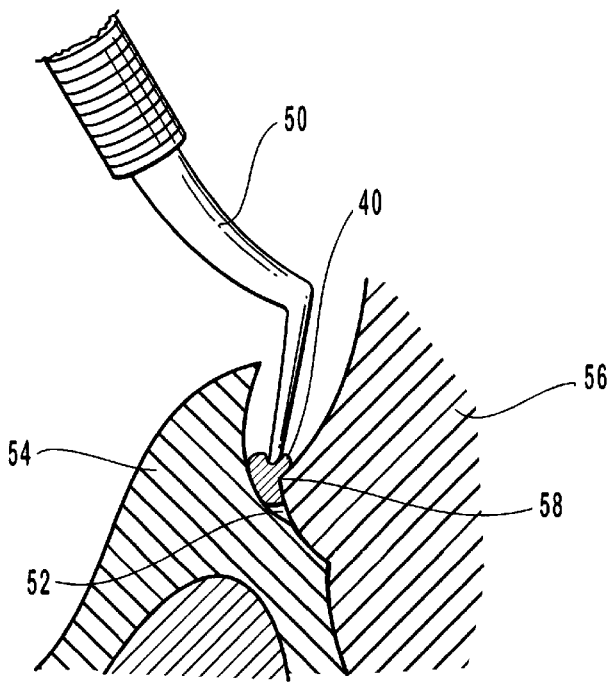
FIG. 6

GINGIVAL RETRACTION CORDS INCORPORATING PROPYLHEXEDRINE

BACKGROUND OF THE INVENTION

1. The Field of the Invention

The present invention relates to gingival retraction cords. More particularly, the invention relates to gingival retraction cords that incorporate propylhexedrine as an improved hemostatic agent and tissue displacing agent, together with optional components, such as one or more astringents or carriers.

2. The Relevant Technology

When performing a variety of dental procedures, it is often desirable to retract gingival tissue in order to prepare a patient's teeth for, e.g., taking dental impressions, placing crowns, performing bridge work, or effecting other dental restorations. A widely used procedure for retracting gingival tissue involves the use of retraction cords which are typically braided or knitted for increased strength, flexibility and resilience.

Examples of braided or knitted gingival retraction cords maybe found in U.S. Pat. No. 4,321,038 to Porteous, U.S. Pat. No. 4,522,933 to Fischer, U.S. Pat. No. 4,617,950 to Porteous et al., and U.S. Pat. No. 4,892,482 to Lococo.

The most common purpose for using a retraction cord is to retract the gingiva away from the tooth in order to take a more accurate and reliable impression of the tooth being restored. It has been found that in order to construct artificial crowns capable of remaining secured to the tooth in a physiologically sound condition and for an extended period of time, it is critical to make an accurate impression of the tooth, particularly in the area at or below the gingival margin. Failure to take an accurate impression can result in a poorly-formed or deficient prosthesis, particularly at the gingival margin. Premature failure of a crown is often due to poor marginal detail in the impression used to fabricate the crown.

The person's gingiva, or "gums", not only prevents an accurate impression of the proper shape of a person's tooth beneath the gingiva, it may also bleed if torn or damaged by high speed cutting drills or burrs used to remove tooth material preparatory to placing a crown. This bleeding may further interfere with the taking of a good impression because extravasated blood tends to prevent adequate cleaning and drying of the marginal area of the tooth prior to taking an impression and tends to displace the impression material before it can set. Thus, the dual problems of contraction of the gingival cuff and the presence of hemorrhaging tissues make it impractical to simply take an impression following shaping of the tooth with a high speed drill or burr without retraction of the gingiva.

In order to control or inhibit the tendency of the gingiva to bleed when physically retracted by the retraction cord and/or if accidentally cut or nicked by the high speed drill or burr, retraction cords are often treated with a hemostatic agent. One type of hemostatic agent includes astringents, which lock or seal off exposed blood vessels so as to arrest bleeding. U.S. Pat. Nos. 4,321,038, 4,522,933, 4,617,950 and 4,892,482, referred to above, discuss the use of astringents such as "alum", or potassium aluminum sulfate.

U.S. Pat. Nos. 4,321,038 and 4,892,402 also discuss the use of epinephrine, which is often used in the form of a salt, typically epinephrine hydrochloride, and which is a known vasoconstrictor. Although epinephrine is commonly used as a vasoconstrictor in a wide variety of applications, the use of epinephrine has the tendency to cause systemic, rather than merely localized, physiological responses. In particular, whereas the topical use of epinephrine may provide a desired hemostatic effect, it is known to produce the side effect of increasing a person's pulse rate and blood pressure. This is not surprising since epinephrine is the principal sympathomimetic hormone produced by the adrenal medulla. Hence, epinephrine is often referred to as "adrenaline", the "fight or flight" hormone, which is associated with fear, excitement, anxiety or other similar emotional and biochemical responses which result in increased pulse rate, elevated blood pressure, and accelerated metabolism. This has in a few cases caused the death of compromised heart heart patients. Nevertheless, it is still commonly used in conventional retraction cords due to the perceived lack of adequate substitutes.

Another drawback of epinephrine is that it is incompatible with the use of iron-based hemostatic agents. In particular, it has been found that epinephrine and ferric iron compounds react to form a purple reaction product. Not only would the reaction of epinephrine and ferric iron-based compounds diminish the activity of both agents, it would also result in a discolored retraction cord which, in turn, would temporarily stain the patient's teeth and gums, as well as the fingers of the dental practitioner attempting to place a retraction cord that included epinephrine and an iron-based hemostatic agent.

In short, it would be an advancement in the art to provide improved gingival retraction cords capable of providing hemostasis without the drawbacks inherent in the use of epinephrine.

More particularly, it would be an important advancement in the art to provide gingival retraction cords that included a vasoconstricting hemostatic agent which did not result in increased pulse rate and elevated blood pressure of the patient.

It would be a further advancement in the art to provide improved hemostatic retraction cords which employed a vasoconstrictor which allowed for the optional inclusion of a wide variety of astringents, including iron-containing compounds, which did not result in the formation of colored reaction products between the vasoconstrictor and the optional astringent.

For example, it would be an advancement in the art to provide a retraction cord which included a vasoconstrictor in combination with an iron-based hemostatic agent which did not result in discoloration of the retraction cord, the patient's teeth and gums, or the fingers of the dental practitioner attempting to place the retraction cord.

Such improved gingival retraction cords for providing hemostasis with a minimum of undesired side effects are disclosed and claimed herein.

SUMMARY AND OBJECTS OF THE INVENTION

The present invention relates to improved gingival retraction cords that have been treated with propylhexedrine and optionally astringents and other active agents. The gingival retraction cords of the present invention provide superior hemostatic and gingiva retraction or displacement properties while avoiding the detrimental side effects of vasoconstrictors such as epinephrine. This is because propylhexedrine has been shown to have a much more localized vasoconstricting effect than epinephrine. Moreover, propylhexedrine is not an adrenal hormone like epinephrine and, hence, does not have the same hormonal effect on a person's biochemistry, pulse and heart rate. By substituting propylhexedrine for epinephrine, it is now possible for the retraction cords according to the present invention to provide superior hemostasis of bleeding gingival tissue by means of a vasoconstrictor having similar vasoconstriction properties compared to epinephrine, but without the systemic side effects of epinephrine, namely, increased heart rate and blood pressure.

The retraction cord may be advantageously "doped" with propylhexedrine by dipping or otherwise soaking the cord in an appropriate solution of propylhexedrine, either alone or in combination with other desired agents. In order to make propylhexedrine more water soluble, it may advantageously be utilized in the form of a salt, such as propylhexedrine hydrochloride. In its salt form, propylhexedrine may be readily dissolved in water or other highly polar solvents such as DMSO, glycerine or alcohol. Propylhexedrine, when not in its salt form, is readily soluble in alcohol, chloroform and ether.

In a preferred embodiment, the retraction cord will include a concentration of propylhexedrine in a range from about 0.01 mg/inch to about 1 mg/inch of the retraction cord, more preferably in a range from about 0.05 mg/inch to about 0.5 mg/inch, and most preferably in a range from about 0.75 mg/inch to about 1.25 mg/inch of the gingival retraction cord.

The desired hemostatic effect of propylhexedrine may be enhanced through the use of one or more auxiliary hemostatic agents such as astringents. A common astringent is alum, which is potassium aluminum sulfate. However, more effective hemostatic agents include a variety of iron compounds, such as ferric sulfate and ferric chloride.

An advantage of propylhexedrine over epinephrine is that propylhexedrine does not react with iron-containing compounds. The result is the ability to derive the full benefit or effect of propylhexedrine and also of iron-containing astringent compounds. Moreover, unlike epinephrine, propylhexedrine does not form colored reaction products with iron-containing compounds. Hence, that retraction cords containing propylhexedrine and iron-containing compounds will not discolor the retraction cord, the patient's teeth and gums, and the fingers of the dental practitioner as could occur if epinephrine were used with ferric astringent compounds.

Preferred retraction cords are knitted in order to provide a superior balance of strength, longitudinal elongation, and transverse resilience. This provides the most effective cord for withdrawing the gingival cuff while exerting the least pain on the patient and providing the greatest ease of placement for the dental practitioner, as discussed full in U.S. Pat. No. 4,522,593 to Fischer.

Accordingly, it is an object of the invention to provide improved gingival retraction cords capable of providing hemostasis without the drawback inherent in the use of epinephrine.

It is a more particular object of the invention to provide gingival retraction cords that include a hemostatic agent which does not result in increased pulse rate and elevated blood pressure of the patient.

It is a further object and feature of the invention to provide hemostatic retraction cords which employ a vasoconstrictor which allows for the optional inclusion of a wide variety of astringents or other hemostatic agents, including iron-containing compounds, which does not result in the formation of colored reaction products between the vasoconstrictor and the optional hemostatic agent.

In a preferred embodiment, it is an object of the invention to provide a retraction cord which includes a vasoconstrictor in combination with an iron-based astringent hemostatic agent which does not result in discoloration of the retraction cord, the patient's teeth and gums, and the fingers of the dental practitioner attempting to place the retraction cord.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 4 illustrates a length of a knitted retraction cord formed using four strands.

FIG. 5 illustrates a transverse cross-section of the knitted retraction cord of FIG. 4 taken along line 4—4 and drawn to a larger scale.

FIG. 6 schematically illustrates a cross-sectional portion of a tooth, associated gingival cuff, and a knitted retraction cord being packed into the gingival sulcus between the tooth and gingival cuff.

DETAILED DESCRIPTION OF THE PREFERRED EMBODIMENTS

I. Introduction

Figure 1:
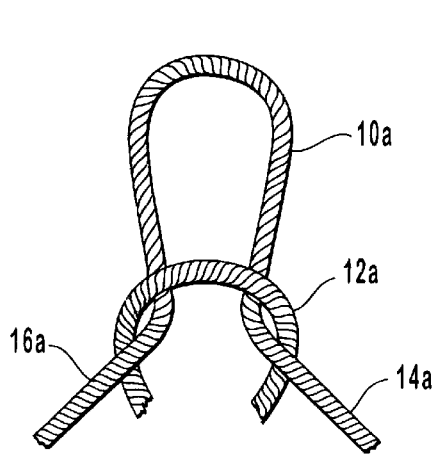
FIG. 1 illustrates an open-loop configuration used in knitting.

The present invention relates to improved gingival retraction cords that have been treated with propylhexedrine to provide hemostasis and retraction or displacement of the gingival cuff. By using propylhexedrine, the gingival retraction cords of the present invention are able to provide superior hemostatic properties without the detrimental side effects caused by vasoconstrictors such as epinephrine. Propylhexedrine has been shown to have a localized vaso-constricting effect when used in gingival retraction cords and does not produce the systemic adrenal effects of epinephrine. In particular, the use of propylhexedrine in a gingival retraction cord does not have the same systemic stimulating effects as epinephrine, which has been found to increase a patient's heart rate and blood pressure when used in retraction cords packed into a person's gingival sulcus.

The retraction cords according to the invention include any of the known retraction cords and may include cords of any material known in the art and any twisted braid and/or knitted patterns known in the art. Examples of different retraction cords within the scope of the invention will be disclosed hereinafter.

The retraction cords maybe soaked, coated, impregnated or otherwise treated with one or more active agents, including propylhexedrine, astringents, carriers and the like. Astringents may be used in order to assist or complement propylhexedrine in providing hemostasis and retraction or displacement of the gingival cuff.

The retraction cords may be manufactured using any known process for braiding, twisting or knitting one or more strands together to form a cord having a desired strength, flexibility and resilience. Similarly, the retraction cords may be used according to procedures known in the art. The only limitation is that the retraction cords according to the invention include a vasoconstrictor such as propylhexedrine that does not cause significant systemic adrenal reactions, such as increased pulse rate and elevated blood pressure.

II. Retraction Cords

The gingival retraction cords according to the present invention may include any retraction cord known in the art so long as it has been treated with propylhexedrine. Examples of suitable gingival retraction cords known in the art are disclosed in U.S. Pat. No. 4,522,593 to Fischer, U.S. Pat. No. 4,321,038 to Porteous, U.S. Pat. No. 4,465,462 to Ticknor, U.S. Pat. No. 4,617,950 to Porteous et al., U.S. Pat. No. 4,871,311 to Hagne, U.S. Pat. No. 4,892,482 to Lococo, U.S. Pat. No. 5,540,588 to Earle and U.S. Pat. No. 5,899,694 to Summer. Of the foregoing patents, U.S. Pat. No. 4,522,593 to Fischer discloses a superior and most preferred retraction cord according to the present invention.

The preferred retraction cords disclosed in U.S. Pat. No. 4,522,593 to Fischer are illustrated in FIGS. 1–6, with FIGS. 1 and 3A and 2 and 3B illustrating alternative, but closely related, embodiments of the knitted retraction cords of Fischer. As used herein, the terms "knitting" and "knitted" relate to a process of using one or more separate strands to form a series of interlocking loops. A "strand" may comprise one or more threads or yarns which are twisted or otherwise joined together.

As more particularly illustrated in FIG. 1, one common type of loop that maybe used to knit the preferred retraction cords according to the present invention is an "open" loop. The "open" loop is formed using a first loop 10a that is interlocked with an adjacent loop 12a such that ends 14a and 16a of loop 10a do not cross one another. The result is a knit pattern more particularly depicted in FIG. 3A.

Figure 2:
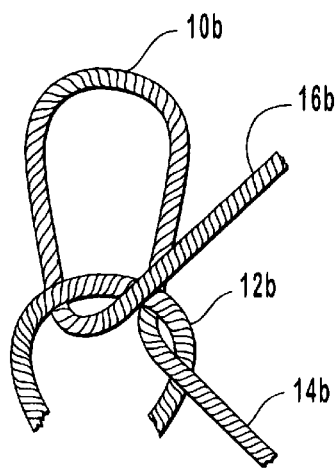
FIG. 2 illustrates a closed-loop configuration used in knitting.

In contrast, FIG. 2 illustrates what is generally known as a "closed" loop because the end 16b of first loop 10b bends back over and crosses in a manner that closes off the loop 10b.

Figure 3A:
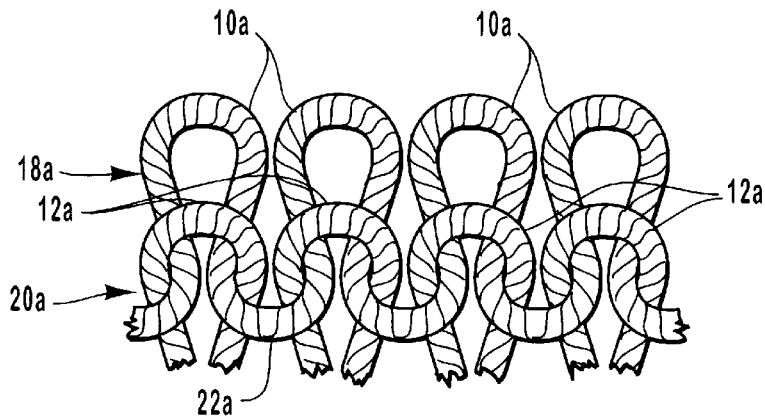
FIG. 3A schematically illustrates the manner in which a single strand of yarn can be knitted using the open-loop configuration of FIG. 1 so as to form a knitted retraction cord from a single strand.

FIG. 3A schematically illustrates two rows (generally designated at 18a and 20a) of interlocked loops constructed utilizing the open-loop configuration shown in FIG. 1. As seen in FIG. 3A, row 18a comprises a plurality of loops 10a, which are interlocked with loops 12a of adjacent row 20a. FIG. 3A illustrates "weft" knitting, which is made from one loop to the next in the same course, or row, of loops, and which can be done using a single strand 22a for row 18a.

Figure 3B:
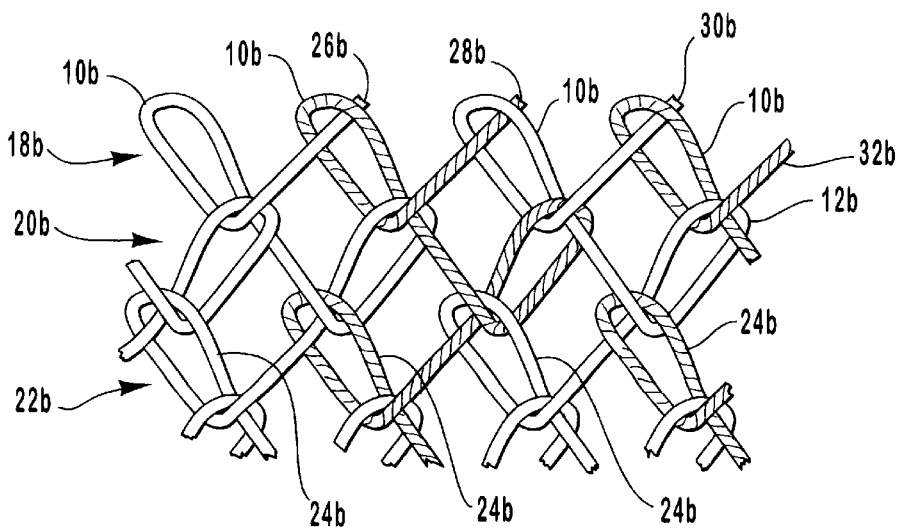
FIG. 3B schematically illustrates the manner in which a plurality of strands may be interlocked and knitted using the closed-loop configuration of FIG. 2 so as to form a knitted retraction cord from several strands.

FIG. 3B alternatively and schematically illustrates three rows (generally designated at 18b, 20b and 22b, respectively) of interlocked loops constructed utilizing the closed-loop configuration of FIG. 2. As seen in FIG. 3A, row 18b comprises loops 10b, which are interlocked with the loops 12b of adjacent row 20b. Loops 12b and row 20b are in turn interlocked with the loops 24b of adjacent row 22b, and so on. FIG. 3B illustrates "warp" knitting in which several strands 24b, 28b, 30b, and 32b, are interconnected such that the interlocking loops of each strand connect from one row to the next.

From the foregoing, it will be appreciated that it is possible to construct a knitted retraction cord 40, as illustrated in FIG. 4, using either the open-loop or closed-loop patterns or systems shown in FIGS. 1–3, or any other suitable knitting pattern. For example, FIG. 4 illustrates a typical knitted retraction cord 40 utilizing four strands of yarn 42, 44, 46 and 48, which are knitted together using the closed-loop pattern illustrated in FIGS. 2 and 3B. This is more readily apparent by reference to FIG. 5, which is a transverse cross-section of FIG. 4 taken along line 4—4 but drawn to a larger scale.

The knitted retraction cord 40 of FIGS. 4 and 5 is characteristically highly elastic and resilient in both the longitudinal and transreverse dimensions. Thus, cord 30 can be easily stretched along its length, and it can also be easily squeezed or compressed radially as hereinafter more fully described. This is so because in a knitted cord the strand or strands are oriented so that a portion of each strand runs transversely, or at approximately right angles to the longitudinal axis of the cord, thus making the cord more compressible and also more stretchable along its length. In contrast, a twisted-strand or braided-type cord has very little longitudinal or transverse elasticity.

In general, as between twisted-strand or braided-type cords, the use of braided retraction cords has been found to be advantageous over twisted-strand cords because the braided cord better maintains its structural integrity under the force of the dental packing instrument and under the pressure exerted by the surrounding gingival tissue once the cord has been packed into the sulcus. Surprisingly, the use of a resilient knitted retraction cord has also been found to be more advantageous still in retracting gingival tissue, despite the fact that its inherent elasticity and resilience might be thought to be detrimental by those used to using braided or twisted-strand retraction cords.

In fact, longitudinal elasticity, or the ability to stretch the retraction cord lengthwise, is extremely beneficial because it avoids the tendency for the packed cord to be dislodged as additional cord is pushed into the sulcus between the tooth and the gingival cuff. As the retractive cord is packed, the "stretch" in the knitted cord permits stress to be placed on the cord without causing already packed portions of the cord to be pulled out of the sulcus.

Transverse resiliency, which can be characterized by the ability of the retraction cord to radially compress and/or bend, is also beneficial when packing a retraction cord into the gingival sulcus. Even if the loops of the knitted retraction cord are left rather loose, because of the intricate interlocking network, there is little or no tendency for the dental packing instrument to slip through the retraction cord. Rather, the compressibility of the knitted cord 40 causes the cord 40 to "dimple" around the edges of the dental packing instrument, such as the dental instrument 50 illustrated in FIG. 6.

As more particularly depicted in FIG. 6, a dental instrument 50 is shown pressing the gingival retraction cord 40 within the sulcus 52 between the gingival cuff 54 and the tooth 56. The resilience and flexibility in the transverse direction allows the knitted retraction cord 40 to conform to irregularities, such as the margin 58 of the tooth 56.

One of the chief advantages of using braided retraction cords has been that the braided cord is not deformed when packed into the sulcus. In contrast, twisted-strand retraction cords tend to flatten out, thereby performing less efficient retraction of the gingival cuff. Thus, it might be expected that a compressible retraction cord would be disadvantageous. However, it has been found that the knitted retraction cords are extremely beneficial for use in retracting gingival tissue, even though knitted cords are more resilient and, thus, more easily compressible, compared to braided cords.

First, because of their compressibility and bendability, there is less tendency of knitted cords to damage underlying gingival tissue as force is applied during packing of the cord by means of a dental instrument. This is because the force of the dental tool tends to be spread out over a larger area by the interlocking loops of the knitted cords. Also, the transverse resilience of the knitted cord 40 enables it to conform (see FIG. 6) to irregularities within the sulcus. Thus, the knitted cord 40 can accomplish both horizontal and vertical retraction using a single cord.

Another advantage of knitted retraction cords is their tendency to return to their original, uncompressed shape because of their resilience. Thus, when a knitted retraction cord is packed into the sulcus, it is compressed, and the "memory" in the retraction cord causes the cord to gently push outward against the gingival tissue. By selecting an appropriate diameter of knitted retraction cord, this outward pushing could significantly increase the ability of the knitted cord to retract gingival tissues over conventional retraction cords. In order to take advantage of this property, it is anticipated that when substituting knitted retraction cords for conventional twisted-strand or braided cords, the diameter of the knitted cord will be larger than the diameter of the conventional cord being replaced. Accordingly, knitted retraction cords will typically have a diameter in a range from about 0.75 to about 1.75 mm, as compared to other retraction cords, which typically have a dimension in a range from about 0.4 to 1 mm. Of course, it is within the scope of the present invention to use cords having any desired diameter.

Another advantage arising from the compressibility of knitted retraction cords is realized when retracting gingival tissue from around the interior of front teeth. The labial or lip-side, gingival tissue around the interior teeth is particularly thin and membranous; more so, for example, than the lingual, or tongue-side, gingival tissue of the interior teeth. Thus, this labial tissue is more susceptible to damage if it is stretched or retracted too far or too fast, resulting in fibrosis, sloughage, and/or formation of scar tissue. Accordingly, it is preferable to avoid too much horizontal retraction. This is more readily accomplished using the knitted retraction cords of the present invention due to their transverse elastically. The lingual gingival tissue can be adequately retracted with the knitted retraction cord only slightly compressed, and by virtue of its compressibility and its ability to stretch and become thinner, the same cord can be packed into the sulcus on the labial side of an interior tooth without over-retracting the gingival tissue. The cord then exerts a general, steady outward force on the tissue, which is desirable.

Another beneficial result of knitted retraction cords is that the interlocking loops result in a substantially increased interstitial volume that is capable of carrying larger amount of chemical agents, such as hemostatic agents and astringents. Additionally, the ability of knitted retraction cords to effectively deliver the chemical agents to the gingival tissue is greatly augmented by the fact that the knitted retraction cords are compressed when packed in the sulcus. Thus, knitted cords may actually express the hemostatic or other agents into the small capillaries of the gingival tissue when compressed, thereby forcing the chemical agents into the bleeding pores so as to stop hemorrhage.

Since one of the aspects of the invention is the importance of delivering propylhexedrine as a hemostatic agent, the ability of the knitted retraction cord to deliver relatively large amounts of such an agent into the sulcus is extremely advantageous. Not only does the enhanced administration of the propylhexedrine permit the knitted retraction cord to be removed after a shorter waiting interval, due to the tissue stiffening and retraction effect of propylhexedrine, but it also results in more uniform administration of the agent and more uniform hemostasis and tissue fixation, thereby permitting a better dental impression to be taken. Moreover, the improved liquid-carrying capacity of knitted retraction cords makes it feasible, if desired, to utilize less absorbent man-made fibers instead of more absorbent cotton fibers necessary when utilizing twisted-strand or braided strand retraction cords. Preferred knitted retraction cords may be obtained from Ultradent Products, Inc., located in South Jordan, Utah.

Notwithstanding the foregoing, it is certainly within the scope of the invention to utilize any retraction cord known in the art, including twisted-strand and braided retraction cords, though such cords may, in many cases, be less preferred than knitted retraction cords, for the reasons set forth above.

III. Hemostatic Agents

The retraction cords according to the present invention may be treated with one or more hemostatic agents, so long as one of the hemostatic agents is propylhexedrine. The term "propylhexedrine", as used in the specification and the appended claims, shall refer to propylhexedrine and any salts or other derivatives of propylhexedrine, including but not limited to propylhexedrine hydrochloride. In addition to propylhexedrine, one or more auxiliary hemostatic agents, such as astringents or other vasoconstrictors, may be used so long as they are compatible with propylhexedrine and do not cause elevated blood pressure and rapid heart beat as does epinephrine.

A. Propylhexedrine

Propylhexedrine is the preferred hemostatic agent because it is able to provide localized hemostasis of hemorrhaging blood vessels without causing the systemic negative size effects caused by retracting cords that deliver epinephrine. The side effects which are eliminated using propylhexedrine include elevated heart rate and quickened pulse. In addition, propylhexedrine is less reactive with astringents such as ferric compounds, which are known to produce purple colored reaction products when mixed with epinephrine. Propylhexedrine has also been found to cause localized stiffening and retraction of gingival tissue, which aids in maintaining reliable retraction of the gingival cuff.

The chemical name for propylhexedrine is N,α-dimethylcyclohexaneethylamine (IUPAC name). It is known as β-cyclohexylisopropylmethylamine in U.S. Pat. No. 2,454,746 to Ullyot, which describes an earlier-used synthetic route for preparing propylhexedrine. Propylhexedrine is represented by the following chemical structure:

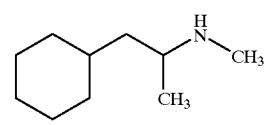

Propylhexedrine is a clear, colorless liquid having a characteristic amine-like odor. It volatilizes slowly at room temperature and solutions are alkaline when subjected to a litmus test. Propylhexedrine therefore absorbs carbon dioxide from the air in an acid-base reaction. The specific gravity is between 0.848 to 0.852. It boils at about 205° C. Propylhexedrine is only slightly soluble in water, with only 1 gram being dissolvable in 500 ml of water. On the other hand, 1 gram of propylhexedrine is soluble in 0.4 ml alcohol, 0.2 ml of chloroform, or 0.1 ml of ether. The hydrochloride form of propylhexedrine, formed by reacting one molar equivalent of propylhexedrine with one molar equivalent of hydrochloric acid, is soluble in water and is a crystalline solid at room temperature.

In order to provide propylhexedrine in a form that is readily absorbed by gingival tissue, it will preferably be in salt form, such as propylhexedrine hydrochloride. In a preferred embodiment, the propylhexedrine will be impregnated into the retraction cord by treating the cord with a 70–80% solution at propylhexedrine dissolved in a mixture of water and alcohol (e.g., ethyl or isopropyl alcohol). Nevertheless, virtually any desired concentration of propylhexedrine may be used so long as it can be used to treat a retraction cord so as to yield a retraction cord doped with a desired level of propylhexedrine.

In addition to providing a hemostatic effect due to its being a vasoconstrictor, propylhexedrine also tends to stiffen and retract the gingival tissue. Therefore, whereas gum tissue is generally soft and pliable such that it can retract and then spring back against the tooth, thereby permitting retraction of the flexible gum tissue away from the tooth as the retraction cord is packed into the sulcus between the gingival cuff and the tooth, once the propylhexedrine has taken effect the retracted gingival cuff will become retracted and stiffened, thereby temporarily fixing the gum tissue in a retracted position. This further assists in taking an accurate impression of the person's tooth. Even though there will be some spring-back of the gum tissue as the retraction cord is removed, full retraction may not occur until the propylhexedrine has substantially worn off.

The amount of propylhexedrine that is administered to a patient's gums is related to the concentration of propylhexedrine that is incorporated within the retraction cord. In view of the fact that different retraction cords may have different thicknesses, densities, and holding properties, the quantity of propylhexedrine associated with different types of retraction cords may differ from cord to cord. Accordingly, the propylhexedrine will preferably be included in a range from about 0.01 mg/inch to about 1 mg/inch of the retraction cord, more preferably in a range from about 0.05 mg/inch to about 0.5 mg/inch, and most preferably in a range from about 0.75 mg/inch to about 1.25 mg/inch of the gingival retraction cord. Retractions cords according to the present invention have been manufactured so as to include propylhexedrine in an amount of 0.1 mg/inch of retraction cord.

B. Astringents

In addition to the propylhexedrine, the inventive gingival retraction cords may include one or more astringents that may assist the propylhexedrine in effecting hemostasis of hemorrhaging gingival tissues. Astringents that may be useful in assisting hemostasis include, but are not limited to, aluminum compounds such as potassium aluminum sulfate, aluminum ammonium sulfate, aluminum sulfate, aluminum chlorohydrate, aluminum acetate, other water soluble astringent aluminum salts, and mixtures thereof. Another class of astringents includes iron-based compositions such as ferric salts, including but not limited to, ferric sulfate, ferric subsulfate, ferric chloride, and mixtures thereof. Other astringents include permangenates, tannins and zinc chloride.

One of the surprising advantages of using propylhexedrine is that, unlike epinephrine, it does not react with and form undesirable reaction products with iron-based compounds such as ferric salts. Epinephrine is known to immediately form purple-colored reaction products when mixed with epinephrine, which not only diminishes the activity and effectiveness of both the epinephrine and the ferric salt but also causes discoloration and staining of the retraction cord which, in turn, can readily stain the patient's teeth and gums as well as the fingers of the dental practitioner attempting to place such a cord. In contrast, propylhexedrine can be freely mixed with a wide variety of astringent salts, including ferric salts, without forming colored reaction products.

When included within the inventive retraction cords, the astringent salts will be included in an amount in a range from about 0.01 mg/inch to about 1 mg/inch of the retraction cord, more preferably in a range from about 0.05 mg/inch to about 0.5 mg/inch, and most preferably in a range from about 0.75 mg/inch to about 1.25 mg/inch of the gingival retraction cord.

Other Vasoconstrictors

Although propylhexedrine is the preferred vasoconstrictor for use with the retraction cords of the present invention, it is within the scope of the invention to include other vasoconstrictors in addition to propylhexedrine, or in place of a portion of the propylhexedrine, in order to provide further hemostasis and/or gum stiffening effect. In order to avoid the problems associated with epinephrine, it is preferable to utilize an auxiliary vasoconstrictor that does not have the negative side effects of epinephrine as outlined above. A wide variety of vasoconstrictors are set forth in U.S. Pat. No. 5,570,141 to Roberts et al. Even though some, or even the majority, of vasoconstrictors identified in Roberts et al. may have similar detrimental effects as epinephrine, to the extent that one or more of such vasoconstrictors is found to provide hemostasis in conjunction with propylhexedrine without causing a significant increase in the patient's heart rate and blood pressure, the use of such vasoconstrictors may be advantageous in combination with propylhexedrine in the gingival retraction cords of the present invention.

IV. Other Components and Agents

It is within the present invention to include any other substance within retraction cords which will facilitate and/or complement the activity of the propylhexedrine, or even to carry out a completely different purpose all together. Such other components may include carriers, which are largely inert, or other active agents.

A. Carriers

In order to soak, impregnate, or otherwise treat the retraction cord with propylhexedrine and other optional agents, it may be useful to dissolve them in one or more carriers. In the case of propylhexedrine, the carrier may include a less polar solvent into which it is readily dissolvable. In the case of propylhexedrine hydrochloride, the carrier may include water or a mixture of water and one or more alcohols. It may be advantageous to utilize a carrier which is not readily volatilized so as to maintain the retraction cord in a moist state when it is desired for the propylhexedrine to be delivered to the person's gums by means of the carrier. On the other hand, it may also be advantageous to utilize a volatile solvent such as water or alcohol, which will dry out, to leave a retraction cord that is dry to the touch. Upon contact with the gums the saliva will act as a temporary carrier in order to draw the propylhexedrine or other active agent out from the retraction cord. Alternatively, the retraction cords maybe wetted with water or other liquid prior to packing the cord within the sulcus.

Suitable liquid carriers other than water include, but are not limited to, alcohols, DMSO, and polyols, such as polyethylene glycol, propylene glycol, polypropylene glycol, dipropylene glycol, glycerine, and sorbitol.

In the case where an astringent is used, the use of the foregoing polyols will intend to reduce the acidic activity of the astringent. For example, it is known that ferric salts are quite acidic and are only effective at relatively low pH (e.g., pH 2). Such a low pH may tend to irritate the person's gingiva. On the other hand, the use of a polyol, while not affecting the pH of the ferric salts, can nevertheless ameliorate or otherwise reduce the acidic activity of the astringent through mechanisms not totally understood. The acidic activity-reducing effect of such polyols is described in U.S. Pat. No. 5,635,162 to Fischer.

B. Other Active Agents

In addition to the foregoing active agents and carriers, it may be useful to include other active agents in order to carry out a desired effect on a person's teeth or gums. For example, it may be advantageous to employ an antimicrobial agent in order to inhibit or prevent infection during placement and withdrawal of the retraction cord in the sulcus between the patient's gingiva and teeth. Similarly, it may be advantageous to utilize anticariogenic agents such as fluoride salts, or remineralizing agents in order to strengthen the remaining portion of the tooth after preparation for receiving a crown. In this way, the remaining "stamp" of the tooth will have increased strength and resistance to infection and decay.

V. Methods of Manufacturing Inventive Retraction Cords

As stated above, it is within the scope of the invention to use any retraction cord known in the art. This includes twisted-strand, braided and knitted retraction cords, although the knitted retraction cords available from Ultradent Products, Inc. located in South Jordan, Utah, are the most preferred retraction cords. Knitted retraction cords are, in general, superior for the reasons set forth above.

Once an appropriate retraction cord has been provided, it is impregnated or otherwise treated with propylhexedrine. In a preferred embodiment, the propylhexedrine is in the form of propylhexedrine hydrochloride, which is dissolved in water or a mixture of water and alcohol (e.g., ethyl alcohol or isopropyl alcohol). Of course, it is within the scope of the invention to apply propylhexedrine in any form and using any desired concentration or solvent system.

Once the retraction cord has been impregnated with the propylhexedrine solution, it is preferably dried so as to yield a dry retraction cord in this way, the propylhexedrine will not bleed out of the retraction cord during spooling, transport and handling prior to use. Nevertheless, it is certainly within the scope of the invention to manufacture moist retraction cords which remain moist after manufacture and during shipping, handling and use. In the case of a dry retraction cord, the use of the more volatile alcohol provides for easier evaporation of the water within the water/alcohol solution (e.g., through the formation of an azeotrope).

The concentration of propylhexedrine hydrochloride (or other desired form of propylhexedrine) in the retraction cord, which is typically measured in milligrams per inch (mg/in.), will generally be a function of the concentration of the propylhexedrine solution as well as the thickness or diameter of the retraction cord. All things being equal, the thicker the retraction cord, the greater will be the amount of propylhexedrine loading of the retraction cord. Accordingly, increasing the thickness of the retraction cord generally increases the concentration of propylhexedrine in terms of milligrams per inch. Similarly, increasing the concentration of the propylhexedrine solution will also increase the milligrams of propylhexedrine per inch of retraction cord, all other things being equal. Retraction cords according to the invention have been manufactured that include propylhexedrine in a concentration of 0.1 mg/inch of retraction cord.

VI. Methods of Using Inventive Retraction Cords

The inventive retraction cords may be used according to any method known in the art. FIG. 6 illustrates a preferred method of utilizing a retraction cord. In particular, FIG. 6 depicts the use of a dental tool 50 used to press a braided gingival retraction cord 40 within the sulcus 52 between the gingival cuff 54 and the tooth 56. In the case where a knitted retraction cord is used, the resilience and flexibility in the transverse direction of the knitted retraction cord allows the cord 40 to conform to irregularities, such as the margin 58 of the tooth 56.

The retraction cord may be sold prewetted or dried. In the case of a prewetted retraction cord, the dental practitioner may wish to utilize gloves so as to avoid contamination of the retraction cord by the fingers of the dental practitioner. In the case of an initially dry retraction cord, the retraction cord may be advantageously used in a dry state. In this case, the mucus found in the gingival tissue may be relied upon to provide at least partial solvation of the propylhexedrine and the optional astringents or other carriers or agents within the retraction cord. In the alternative, the dry retraction cords may be moistened with water or other appropriate liquid just prior to use in order to "activate" the initially dry components on the retraction cord so as to facilitate their migration from the retraction cord into the gingival tissue in order to effect their desired hemostatic and tissue-stiffening and retraction effects.

Finally, a gingival retraction cord which only includes propylhexedrine may be advantageously dipped in an astringent solution just prior to application into the sulcus so as to provide the benefits of both propylhexedrine and the astringent without having premixed them prior to application onto the retraction cord. It is also within the scope of the invention to apply propylhexedrine and any auxiliary components chair-side by the dental practitioner prior to packing the retraction cord into the sulcus of the patient.

VII. Summary

The present invention provides improved gingival retraction cords capable of providing hemostasis without the drawback inherent in the use of epinephrine.

The present invention more particularly provides gingival retraction cords that include a hemostatic agent, namely propylhexedrine, which does not result in increased pulse rate and elevated blood pressure of the patient.

The invention further provides hemostatic retraction cords which employ a vasoconstrictor, namely propylhexedrine, which allows for the optional inclusion of a wide variety of astringents or other hemostatic agents, including iron-containing compounds, which does not results in the formation of colored reaction products between the vasoconstrictor and the optional hemostatic agent, as would occur when using epinephrine.

In a preferred embodiment, the present invention provides a retraction cord which includes a vasoconstrictor in combination with an iron-based astringent hemostatic agent which does not result in discoloration of the retraction cord, the patient's teeth and gums, and the fingers of the dental practitioner attempting to place the retraction cord.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A fiber-based carrier for providing hemostatic retraction of gingival tissue comprising:

a gingival retraction cord; and propylhexedrine carried with the gingival retraction cord in an amount effective to provide hemostasis when the retraction cord is placed in contact with gingival tissue.

2. A fiber-based carrier as defined in claim 1, wherein the gingival retraction cord comprises multiple strands braided or twisted together.

3. A fiber-based carrier as defined in claim 1, wherein at least a portion of the gingival retraction cord comprises cotton.

4. A fiber-based carrier as defined in claim 1, wherein the gingival retraction cord comprises at least one strand formed into a plurality of interlocking loops so as form a knitted retraction cord, said cord being knitted sufficiently loosely such that it is elastic in a longitudinal dimension so as to be able to be stretched and resilient in a transverse dimension.

5. A fiber-based carrier as defined in claim 1, wherein the gingival retraction cord is impregnated with the propylhexedrine.

6. A fiber-based carrier as defined in claim 1, wherein the gingival retraction cord is at least surface coated with the propylhexedrine.

7. A fiber-based carrier as defined in claim 1, further including an astringent associated with the retraction cord.

8. A fiber-based carrier as defined in claim 7, wherein the astringent is at least one of potassium aluminum sulfate, ammonium aluminum sulfate, aluminum sulfate, aluminum acetate, aluminum chlorohydrate, other water soluble aluminum salts, zinc chloride, permanganates or tannins.

9. A fiber-based carrier as defined in claim 7, wherein the astringent is at least one of ferric sulfate, ferric subsulfate, ferric chloride, or other water soluble ferric salts.

10. A fiber-based carrier as defined in claim 9, further including a polyol associated with the retraction cord in an amount effect so as to reduce acidic activity of the astringent.

11. A fiber-based carrier as defined in claim 1, wherein the propylhexedrine is included in amount in a range of about 0.01 mg/inch to about 1 mg/inch of the retraction cord.

12. A fiber-based carrier as defined in claim 1, wherein the propylhexedrine is included in amount in a range of about 0.05 mg/inch to about 0.5 mg/inch of the retraction cord.

13. A fiber-based carrier as defined in claim 12, where the propylhexedrine is in the form of propylhexedrine hydrochloride.

14. A fiber-based carrier as defined in claim 1, wherein the propylhexedrine is included in amount in a range of about 0.75 mg/inch to about 1.25 mg/inch of the retraction cord.

15. A fiber-based carrier as defined in claim 1, wherein the propylhexedrine is in the form of a salt of propylhexedrine.

16. A retraction system for providing hemostatic retraction of gingival tissue comprising:

a gingival retraction cord;

propylhexedrine carried with the gingival retraction cord in an amount effective to provide hemostasis when the retraction cord is placed in contact with gingival tissue; and an astringent.

17. A retraction system as defined in claim 16, wherein the gingival retraction cord comprises at least one strand formed into a plurality of interlocking loops so as form a knitted retraction cord, said cord being knitted sufficiently loosely such that it is elastic in a longitudinal dimension so as to be able to be stretched and resilient in a transverse dimension.

18. A fiber-based carrier as defined in claim 16, wherein the propylhexedrine is included in amount in a range of about 0.01 mg/inch to about 1 mg/inch of the retraction cord.

19. A retraction system for providing hemostatic retraction of gingival tissue comprising:

a gingival retraction cord;

propylhexedrine carried with the gingival retraction cord in an amount effective to provide hemostasis when the retraction cord is placed in contact with gingival tissue; and an iron-based astringent.

20. A fiber-based carrier as defined in claim 19, wherein the propylhexedrine is included in amount in a range of about 0.01 mg/inch to about 1 mg/inch of the retraction cord.

* * * * *

UNITED STATES PATENT AND TRADEMARK OFFICE
CERTIFICATE OF CORRECTION

PATENT NO. : 6,375,461 B1
DATED : April 23, 2002
INVENTOR(S) : Steven D. Jensen and Dan E. Fischer It is certified that error appears in the above-identified patent and that said Letters Patent is hereby corrected as shown below:

Column 1,
Line 23, before "found in" change "maybe" to -- may be --

Column 2,
Line 14, before "heat patients" delete "heart"

Column 5,
Line 5, after "The retraction cord" change "maybe" to -- may be --
Line 40, after "more threads or" change "yams" to -- yarns --

Column 6,
Line 11, before "42, 44, 46 and 48" change "yams" to -- yarns --

Column 11,
Line 27, after "the remaining" change "stamp" to -- "stump" --
Line 48, after "dry retraction cord" please insert -- . --
Line 48, before "this way," change "in" to -- In --

Column 12,
Line 56, before "in the formation" change "results" to -- result --

Signed and Sealed this

Eleventh Day of February, 2003

JAMES E. ROGAN
*Director of the United States Patent and Trademark Office*